(12) United States Patent
Chao et al.

(10) Patent No.: US 7,940,368 B2
(45) Date of Patent: May 10, 2011

(54) STRUCTURE OF POLARIZING TERAHERTZ WAVE DEVICE

(75) Inventors: Ru-Pin Chao, HsinChu (TW); Ci-Ling Pan, Hsin-Dian (TW); Cho-Fan Hsieh, Luodong Town, Yilan County (TW); Yu-Chien Lai, Dacun Township, Changhua County (TW)

(73) Assignee: National Chiao Tung University, Hsin-Chu (TW)

( * ) Notice: Subject to any disclaimer, the term of this patent is extended or adjusted under 35 U.S.C. 154(b) by 265 days.

(21) Appl. No.: 12/243,734

(22) Filed: Oct. 1, 2008

(65) Prior Publication Data
US 2010/0053538 A1    Mar. 4, 2010

(30) Foreign Application Priority Data
Aug. 27, 2008  (TW) ............................ 97132755 A

(51) Int. Cl.
*G02F 1/13* (2006.01)
*G02B 5/30* (2006.01)

(52) U.S. Cl. ........................................ 349/194; 359/496

(58) Field of Classification Search ........................ None
See application file for complete search history.

(56) References Cited

U.S. PATENT DOCUMENTS

| 3,364,433 A | * | 1/1968 | Freund et al. | 330/4.6 |
| 4,214,819 A | * | 7/1980 | Pohl et al. | 349/23 |
| 4,564,266 A | * | 1/1986 | Durand et al. | 349/177 |
| 5,184,233 A | * | 2/1993 | Lim et al. | 349/166 |
| 2009/0002581 A1 | * | 1/2009 | Chao et al. | 349/23 |

OTHER PUBLICATIONS

C-Y Chen et al. Liquid-crystal-based terahertz tunable Lyot filter. Applied Physics Letters 88, 101107, Mar. 2006.*
C-S Yang et al. The complex refractive indices of the liquid crystal mixture E7 in the THz frequency range. Advance posting in Journal of Optical Society of America B, document ID 130294 (retrieved from www.opticsinfobase.org/josab/upcoming_pdf.cfm?id=130294), posted Jul. 2010.*
C-F Hsieh et al. Polarizing terahertz waves with nematic liquid crystals. Optics Letters, 33:11:1174, Jun. 2008.*
J.C. Martinez-Antón et al. High performance Feussner-type polarizers based on stretched poly(ethylene-terephthalate) films. Applied Physics Letters, 80:10:1692, Mar. 2002.*

* cited by examiner

*Primary Examiner* — Mike Stahl
(74) *Attorney, Agent, or Firm* — Birch, Stewart, Kolasch & Birch, LLP

(57) ABSTRACT

The Terahertz Polarizer structure of the present invention comprises of: A pair of parallel quartz layers for forming a rectangular cube with internal space, then a birefringent liquid crystal is placed in the internal space and sealed, and a pair of permanent magnets with reverse polarities are placed at both sides of the pair of fused silica layers.

13 Claims, 6 Drawing Sheets

STRUCTURE OF POLARIZING TERAHERTZ WAVE DEVICE

FIELD OF THE INVENTION

The present invention relates to a Terahertz Polarizer structure, it specifically relates to Terahertz Polarizer structure that uses birefringent liquid crystal as polarizing component.

BACKGROUND OF THE INVENTION

In the so-called terahertz wavelength range, 1 THz=$10^{12}$ Hz; it is between infrared and microwave and includes part of millimeter wavelength (0.1 THz) to far infrared region (25 THz) as shown in FIG. 1; in other words, it is between two major zones that are based on electron and photon as the development means. In the research field of solid state physics, terahertz wavelength range is a very important spectrum because many important material characteristics energy correspond to THz wave range, for example, acceptor and donor in semiconductor, the binding energy of exciton, optical phonon, superconducting energy gap, etc. All of them fall in these wavelength section; moreover, it has very great development potential in the fields of spectral analysis, radio astronomy, telemetry, communication and biomedical science.

There are two major ways to generate terahertz radiation, namely, current surge model or photoconduction model and secondary nonlinear optical rectification model. Among them, current surge model is the generation of radiation when the optically excited carriers are accelerated by externally applied electric field, that is, it is the dipole radiation generated when photo transient is changed; however, this method is limited by the characteristic and design of the used photoconductive antenna, as well as the sensitivity of the receiver, hence, the radiation power of the terahertz electromagnetic wave system is thus restricted; in secondary nonlinear optical rectification model, the incident ultra-short optical pulse is coupled with the nonlinear polarization coefficient of the crystal so as to synthesize terahertz electromagnetic wave; however, a polarizer is needed in this method.

FIG. 2 illustrates the prior art metal wire grid polarizer structure. The prior art polarizer is mainly metal line grating polarizer 20, with its principle based on the light reflection and the transmission; that is, array is made on the transparent substrate 21, and this array is formed by closely spaced the parallel metal lines 22; therefore, the preparation of metal line grating polarizer will need to use micro-processing techniques such as metal deposition and etching that involves multi-layer metals; however, metal line grating polarizer prepared in this way not only has the disadvantage of high cost, but also the metal line can easily get damaged.

SUMMARY OF THE INVENTION

One objective of the present invention is to provide a Terahertz Polarizer structure, which can use birefringent liquid crystal as polarization component to replace metal line processed metal grating polarizer; the major advantages are the reduction of the cost and rigid configuration.

One objective of the present invention is to provide a Terahertz Polarizer structure, including: a pair of parallel quartz pieces that form a gap having the birefringent liquid crystal layer filled in the gap, and a pair of permanent magnets of reverse polarity that are placed at both sides of the pair of quartz pieces.

One objective of the present invention is to provide a Terahertz Polarizer structure, including: It is made up of material of fused silica with refractive index about 1.95 in the terahertz frequency range, then a pair of parallel fused silica prisms are used to form a rectangular cube that is of 22.3 mm in length, 15 mm in width and 15 in height; within the rectangular cube, a gap if formed with an angle between 55 to 60 degrees to the edge of the rectangular cube with better angle about 56±0.5; the gap is filled with liquid crystal molecules with refractive indexes $n_o$, $n_e$ of respectively 1.58, 1.71 to prepare liquid crystal layer of thickness in the range of 0.70 to 2.00 mm; finally, Teflon sheet is used to seal it to prevent the leakage of the liquid crystal. Under o-ray and e-ray, the corresponding total internal reflection angles are 54.12 and 61.27 degrees, respectively. Furthermore, a pair of permanent magnets that is made up of sintered Nd—Fe—B but of reverse polarity and are able to provide magnetic field of 0.2 tesla are placed at both sides of the pair of quartz pieces.

Another objective of the present invention is to provide a Terahertz Polarizer structure, including: First and second fused silica prisms. Each of the fused silica prism includes a right-angled triangle formed by a bottom surface, a vertical surface and a slope surface and a pair of side surfaces that are located respectively at both sides of right-angled triangle, wherein two slope surfaces face and parallel to each other, and the birefringent liquid crystal layer in placed inside; moreover, a pair of permanent magnets with reverse polarity are placed respectively at the external sides of the pair of side surfaces; and an optical source placed at the external side of the bottom surface of the first fused silica prism so as to be used as enter plane for the THz wave, then THz signals pass through liquid crystal layer, and finally to leave from the bottom surface of the second quartz prism.

DETAILED DESCRIPTION OF THE INVENTION

In the followings, different embodiments are used to describe the present invention; the described compositions, arrangements and steps, etc. are used to describe the embodiment content and are only examples instead of using to limit the present invention. In addition, in the disclosed content, the use of "and/or" is for briefing purpose; the descriptions of "cover" or "above" can include the direct contact and non-direct contact.

Figure 1:
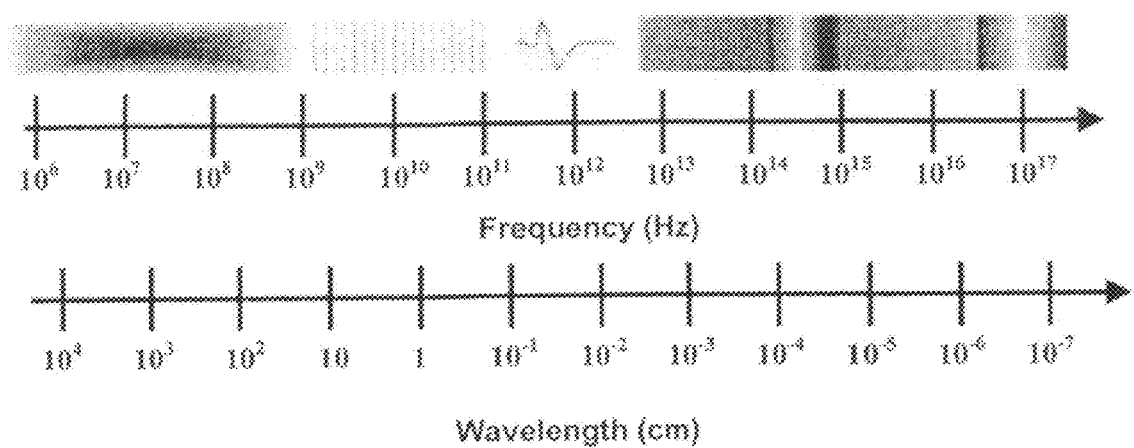
FIG. 1 illustrates the wavelength and frequency relationship of electromagnetic wave.
Figure 2:
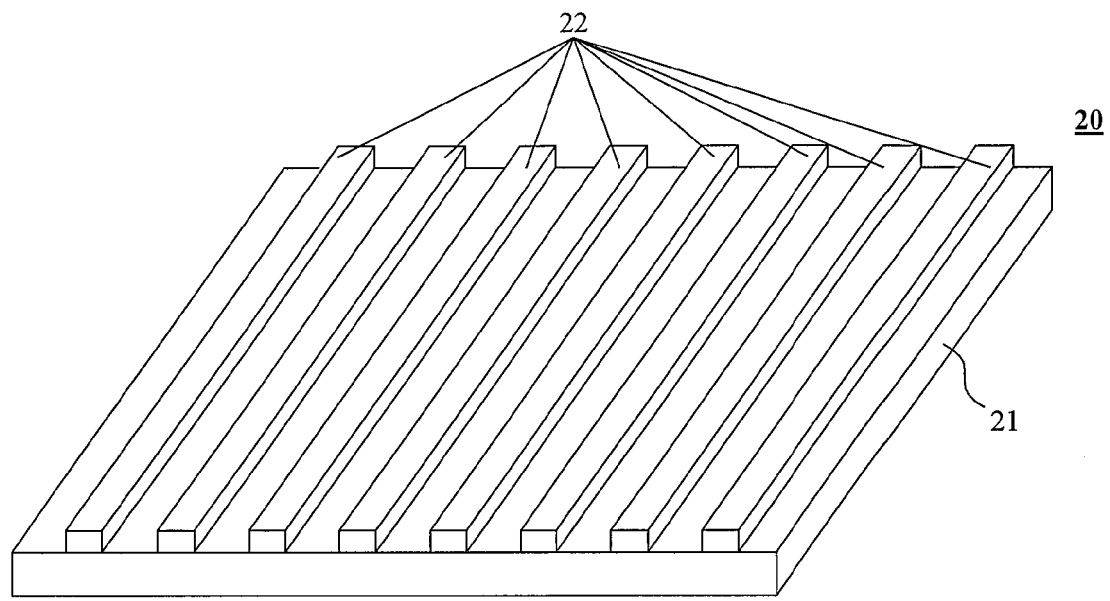
FIG. 2 illustrates the prior art metal line grating polarizer structure.
Figure 3:
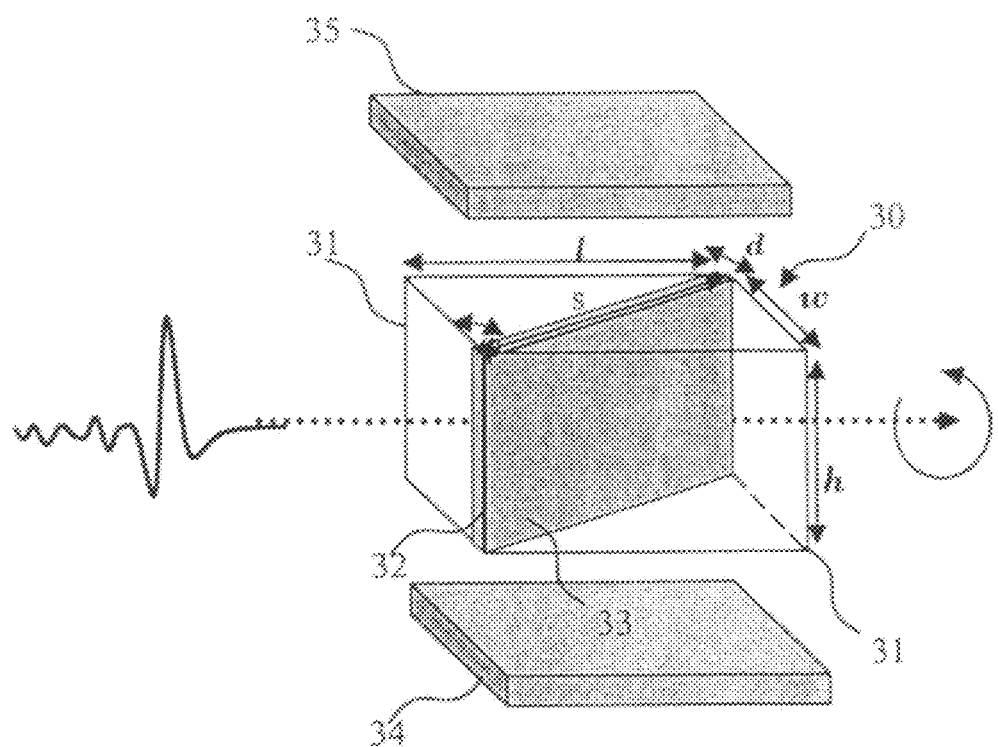
FIG. 3 illustrates Terahertz Polarizer structure of the present invention.

As shown in FIG. 3, it is an illustration of the Terahertz Polarizer structure of the present invention; fused silica material is used to prepare right-angled triangle fused silica prism 31, and each triangular fused silica prism 31 has a long side 1, wide side w, high side h and slope side s; therefore, two slope sides s and two wide sides w form a slope surface, two wide sides w and two high sides h form a bottom surface, two long sides l and two high sides h form a vertical surface, and a pair of symmetrical side surfaces that are formed by long side l, wide side w and slope side s; among them, 90 degree angle is formed between bottom surface and vertical surface, an angle φ from 55 to 60 degrees is formed between bottom surface and slope surface; furthermore, a pair of side surfaces and a right-angled triangle formed by bottom surface, vertical surface and slope surface will together form a triangular fused silica prism 21.

Two slope sides s of two triangular fused silica prisms 31 are parallel to each other with appropriate gap d to form rectangular cube 30 (l×(w+d)×h); moreover, within the rectangular cube, there is a slope trench 32 that is formed by high side h, slope side s and gap d; therefore, trench 32 has an angle φ with the bottom surface of any triangular fused silica prism; moreover, trench 32 is injected with birefringent liquid crystal material with $n_e > 1.62$ and $n_o < 1.61$, wherein $n_o$ is defined as the refractive index of liquid crystal when the polarization direction of the incident light is vertical to the long axis of liquid crystal; $n_e$ is the refractive index of liquid crystal when the polarization direction of the incident light is parallel to the long axis of liquid crystal; furthermore, Teflon piece is used as blocking piece to the peripherals of liquid crystal material to seal it so that liquid crystal layer 33 is formed. Both the left and right sides (the side surface formed by long side l, wide side and gap d) of rectangular cube 30 are installed with a pair of permanent magnets 34, 35 with reverse polarity, then through this pair of permanent magnets 34, 35 of reverse polarity, the liquid crystal molecules 33 can be stably arranged.

In the present embodiment, the quartz piece used is made up of fused silica with long side l of 22.3 mm, wide side w of 15 mm and high side h of 15 mm; the refractive index of this quartz material is 1.95 with angle φ about 56±0.5 degree; and the fused silica prism 31 forms a right-angled triangle. Place two triangular fused silica prisms 31 together with a gap d from 0.70 to 2.00 mm, let the slope surfaces of two fused silica prisms 31 be parallel to each other to form a rectangular cube 30 with central trench 32. Then liquid crystal molecules with refractive indexes $n_o$, $n_e$ of respectively 1.58, 1.71 are filled into the trench 32, then Teflon piece is used as blocking material to seal the peripherals of the trench 32 to prevent liquid crystal molecules from leaking out, and liquid crystal layer 33 with birefringence is formed; moreover, the total reflection angles of o-ray and e-ray between the quartz piece and the liquid crystal are 54.12 and 61.27 degrees, respectively. Furthermore, a pair of permanent magnets, sintered in Nd—Fe—B with magnetic field strength 0.2 Tesla but of north and south pole respectively in the magnetic polarities, are installed at both sides of rectangular cube 30.

Figure 4:
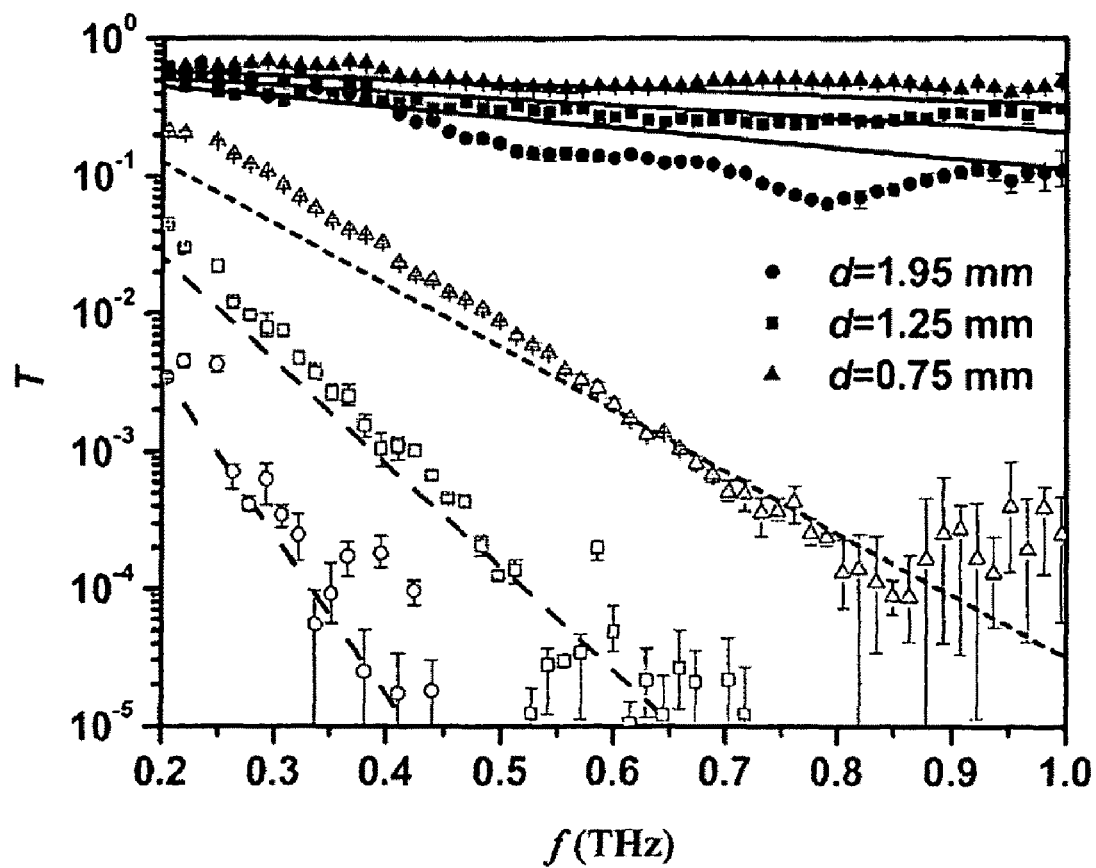
FIG. 4 illustrates the transmission-frequency chart of the experimental results and theoretic predictions of different gaps in the present invention.
Figure 5:
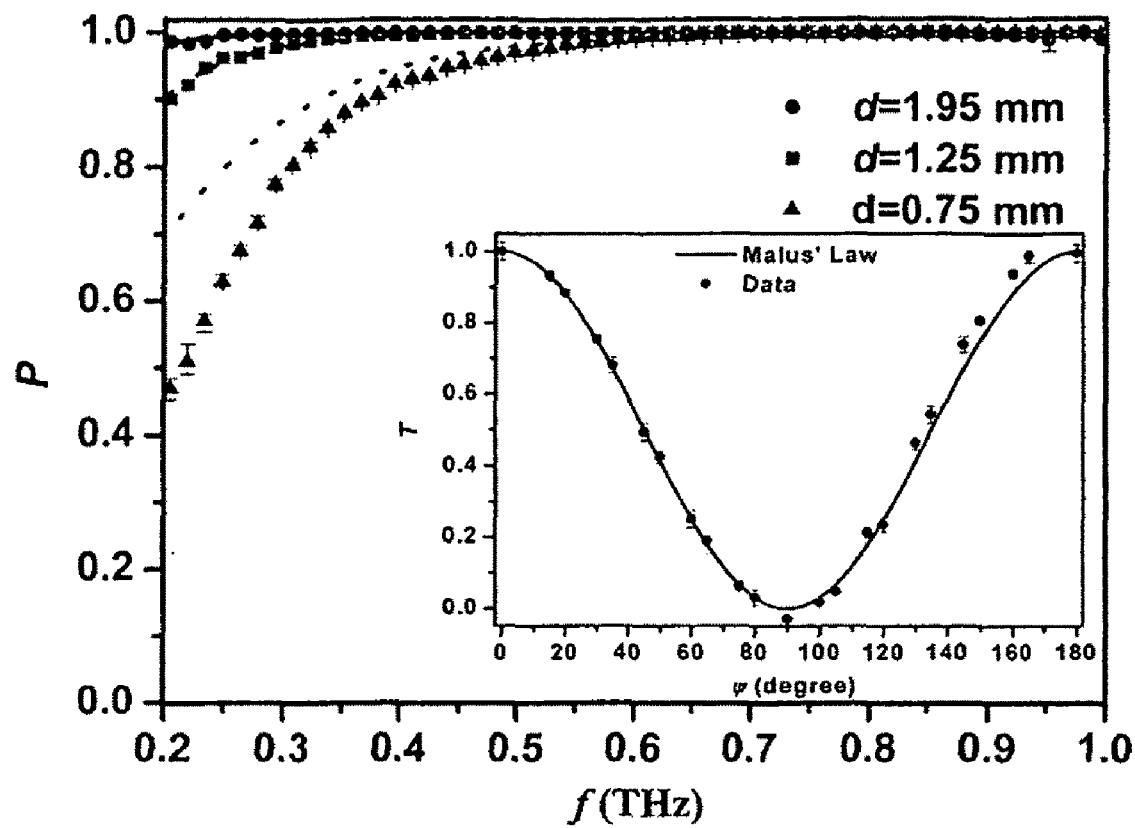
FIG. 5 illustrates the polarization factor-frequency chart of the experimental results and theoretic predictions of different gaps in the present invention.
Figure 6:
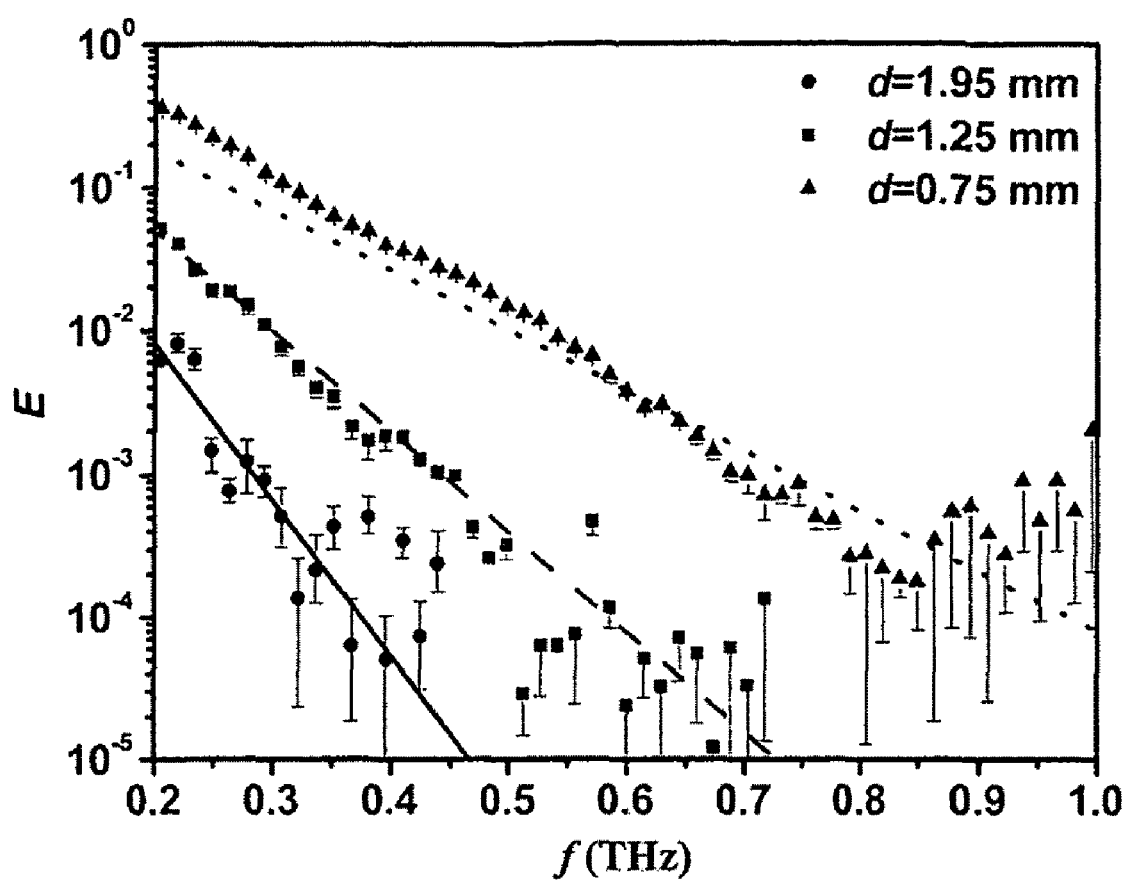
FIG. 6 illustrates the extinction ratio-frequency chart of the experimental results and theoretic predictions of different gaps in the present invention.

Please refer at the same time from FIG. 4 to FIG. 6, which shows the adjustment of gap sizes in the above mentioned embodiment of the present invention; here triangle, square, and circle represent respectively at d=0.75 mm, 1.25 mm and 1.95 mm, the optical light source that generates optical wave (not shown in the figure) is placed at the bottom surface of one of the fused silica prisms, hence, optical wave will enter through bottom surface of the fused silica prism, then it will pass through liquid crystal layer and leaves from the bottom surface of another fused silica prism; moreover, based on the experimental results, the following charts are plotted, namely, transmission-frequency chart, polarization factor-frequency chart and extinction ratio-frequency chart. The dots in FIG. 4 are experimental values, solid line and dotted line are used respectively to describe the theoretical calculations of transmissions at o-ray and e-ray, which explains that the current design can be utilized in broadband terahertz wavelength; FIG. 5 describes the relationship between polarization factor versus frequency, under perfect polarizer condition, the polarization factor must be 1; the inserted drawing shows the transmittance after the rotation of this design, the theoretical curve is Y=cos 2X; FIG. 6 shows a relationship between extinction ratio versus frequency, and under perfect polarizer condition, extinction coefficient is zero.

Although the present invention is disclosed through a better embodiment as above, yet it is not used to limit the present invention, anyone that is familiar with this art, without deviating the spirit and scope of the present invention, can make any kinds of change, revision and finishing; therefore, the protection scope of the present invention should be based on the scope as defined by the following attached "what is claimed".

What is claimed is:

1. A Terahertz Polarizer structure, comprising:
a first fused silica prism and a second fused silica prism, each of the first and second fused silica prisms including a right-angled triangular prism that is formed by a bottom surface, a vertical surface, a hypotenuse surface and a pair of mutually parallel side surfaces that are perpendicular to each of the bottom surface, the vertical surface and the hypotenuse surface, wherein the hypotenuse surface of the first fused silica prism and the hypotenuse surface of the second fused silica prism are disposed parallel to each other and are separated by a gap;
a liquid crystal layer with birefringence is filled within the gap;
two permanent magnets with reverse polarities respectively placed at an external side of one of the pair of side surfaces of each of the first and second fused silica prisms and at an external side of the other one of the pair of side surfaces of each of the first and second fused silica prisms; and
an optical source, placed at an external side of the bottom surface of the first fused silica prism;
wherein the optical source generates an optical wave to enter through the bottom surface of the first fused silica prism, then to pass through the liquid crystal layer and to leave from the bottom surface of the second fused silica prism.

2. The Terahertz Polarizer structure of claim 1, wherein the bottom surface and the vertical surface are perpendicular to each other.

3. The Terahertz Polarizer structure of claim 1, further including a blocking element that is placed at a peripheral of the liquid crystal layer.

4. The Terahertz Polarizer structure of claim 3, wherein the blocking element is a TEFLON piece.

5. The Terahertz Polarizer structure of claim 1, wherein the gap is from 0.70 to 2.00 mm.

6. The Terahertz Polarizer structure of claim 1, wherein the liquid crystal layer has $n_e > 1.62$ and $n_o < 1.61$.

7. The Terahertz Polarizer structure of claim 1, wherein the birefringence is 0.13.

8. The Terahertz Polarizer structure of claim 1, wherein two permanent magnets are made of a sintered material.

9. The Terahertz Polarizer structure of claim 8, wherein the sintered material is Nd—Fe—B sintered matter.

10. The Terahertz Polarizer structure of claim 1, wherein the magnetic field strength of each permanent magnet is at least 0.2 Tesla.

11. The Terahertz Polarizer structure of claim 1, wherein the gap and a rectangular cube defined by the first and second fused silica prisms form an angle from 55 to 60 degrees.

12. The Terahertz Polarizer structure of claim 11, wherein the bottom surface and the hypotenuse surface form an angle from 55 to 57 degrees.

13. The Terahertz Polarizer structure of claim 1, wherein the first and the second fused silica prisms and the liquid crystal layer have corresponding internal total reflection angles of 54.12 and 61.27 degrees for o-ray and e-ray, respectively.

* * * * *